United States Patent [19]

Loveless

[11] 4,074,367
[45] Feb. 21, 1978

[54] PROSTHETIC LOAD-LIFT HOOK LOCKING MECHANISM

[75] Inventor: John H. Loveless, Silver Spring, Md.

[73] Assignee: The United States of America as represented by the Administrator of Veterans' Affairs, Washington, D.C.

[21] Appl. No.: 724,062

[22] Filed: Sept. 16, 1976

[51] Int. Cl.$^2$ .................... A61F 1/00; A61F 1/06
[52] U.S. Cl. .................................. 3/1.1; 3/12.3
[58] Field of Search .................. 3/1.1, 1.2, 12-12.8

[56] References Cited

U.S. PATENT DOCUMENTS

| | | | |
|---|---|---|---|
| 2,580,987 | 1/1952 | Alderson | 3/1.1 |
| 3,866,246 | 2/1975 | Seamone et al. | 3/1.1 |

FOREIGN PATENT DOCUMENTS

| | | | |
|---|---|---|---|
| 106,661 | 9/1924 | Switzerland | 3/12.3 |

Primary Examiner—Ronald L. Frinks

Attorney, Agent, or Firm—Browdy and Neimark

[57] ABSTRACT

An electrically controlled pawl and ratchet mechanism on a prosthetic device to increase the lifting ability of the system throughout the excursion range thereof and without opening the system's terminal device. A ratchet wheel is positively connected to and driven by the forearm pulley assembly of the prosthetic system and an electrically controlled pawl is used therewith to provide uni-directional braking action, which inhibits opening of the associated terminal device. The device is self-locking on engagement of the pawl with the ratchet wheel under torque application conditions. Reduction of the applied torque to zero subsequently causes disengagement of the pawl, and the terminal device may then be freely used. The pawl is controlled by a solenoid which is energized for a timed period by a timer operated responsive to command energization of the system motor.

7 Claims, 3 Drawing Figures

PROSTHETIC LOAD-LIFT HOOK LOCKING MECHANISM

FIELD OF THE INVENTION

This invention relates to artificial limbs, and more particularly to a ratchet and pawl device which may be employed to control the hook portion of an artificial arm so that it will not open during the lifting of a load.

BACKGROUND OF THE INVENTION

Various prosthetic systems have been designed employing myoelectrically controlled and similarly controlled power units. Included in such systems are those which provide powered elbow action, nameley, elevation of a forearm portion provided with a hook assembly for grasping and lifting a load. With existing devices of this type there is only a minimal live-lift capacity, that is, there is a lack of ability to grasp an object weighing one-half pound or more and lift it throughout the total elbow excursion range without opening the terminal device and releasing the object. This is also true of conventional body-powered prosthesis units currently in use.

Thus, there is a substantial need for an attachment or built-in device employed with a prosthetic unit to provide the ability to operate the prosthetic elbow without opening the associated terminal device or hook for grasped objects of substantial weight, for example, objects weighing up to three pounds or more.

More specifically, there is a substantial need for a reliable means for automatically locking the terminal device or hook in a closed grasping condition during the total excursion range of the powered lifting stage of the associated forearm member, and for afterwards releasing the terminal device for normal operation.

SUMMARY OF THE INVENTION

Accordingly, a main object of the invention is to provide for an improved prosthetic device.

Another object is to overcome defects in the prior art, such as indicated above.

Yet another object is to provide a prosthetic device which holds the hook portion of an artificial arm substantially locked during the powered lifting movement of the associated forearm member and releases said hook portion upon completion of the lifting movement, the device being relatively simply in construction, being easy to install on existing prosthetic units, and enabling the user to lift relatively heavy objects without risk of opening the hook portion during the lifting action.

A further object of the invention is to provide an improved electrically operated pawl and ratchet device attached to the forearm pulley assembly of an artificial arm unit and operated as an automatic uni-directional brake to lock the associated terminal device or hook in grasping condition during the powered lifting excursion of the forearm member of the unit, whereby to allow a relatively heavy object to be held dependably during the total elbow excursion range of lifting action, and thereafter releasing the pulley assembly to allow opening of the hook, the device involving relatively simple and inexpensive components, being compact in size, being light in weight, and being reliable in operation.

A still further object of the invention is to provide an improved automatic pawl-and-ratchet holding device for the terminal or hook portion of a cable-operated powered prosthesis unit, the holding device acting as a uni-directional brake preventing opening of the terminal or hook portion during lifting action, and the geometry of the pawl and ratchet assembly being such that once the pawl element is momentarily engaged and torque is applied to the associated forearm member, the pawl and ratchet assembly will be self-locking and will not disengage until the applied torque is reduced to zero.

A still further object of the invention is to provide an improved electrically operated automatic pawl-and-ratchet locking and holding device for the terminal or hook portion of an electrically powered prosthesis unit, the holding device being automatically timed for locking action responsive to the energization of the associated driving motor and terminating its locking signal for enabling release of the terminal or hook portion at the end of a time period sufficient to substantially complete the desired powered lifting action of the associated elbow assembly, the terminal or hook portion being essentially disconnected from the driving motor during the elbow lifting action so that the weight of an object that can be lifted is limited only by the frictional grasp of the hook and the torque capability of the driving motor.

BRIEF DESCRIPTION OF THE DRAWINGS

Further objects and advantages of the invention will become apparent from the following detailed description of an embodiment, and from the accompanying drawing thereof, wherein.

DESCRIPTION OF A PREFERRED EMBODIMENT

Figure 1:
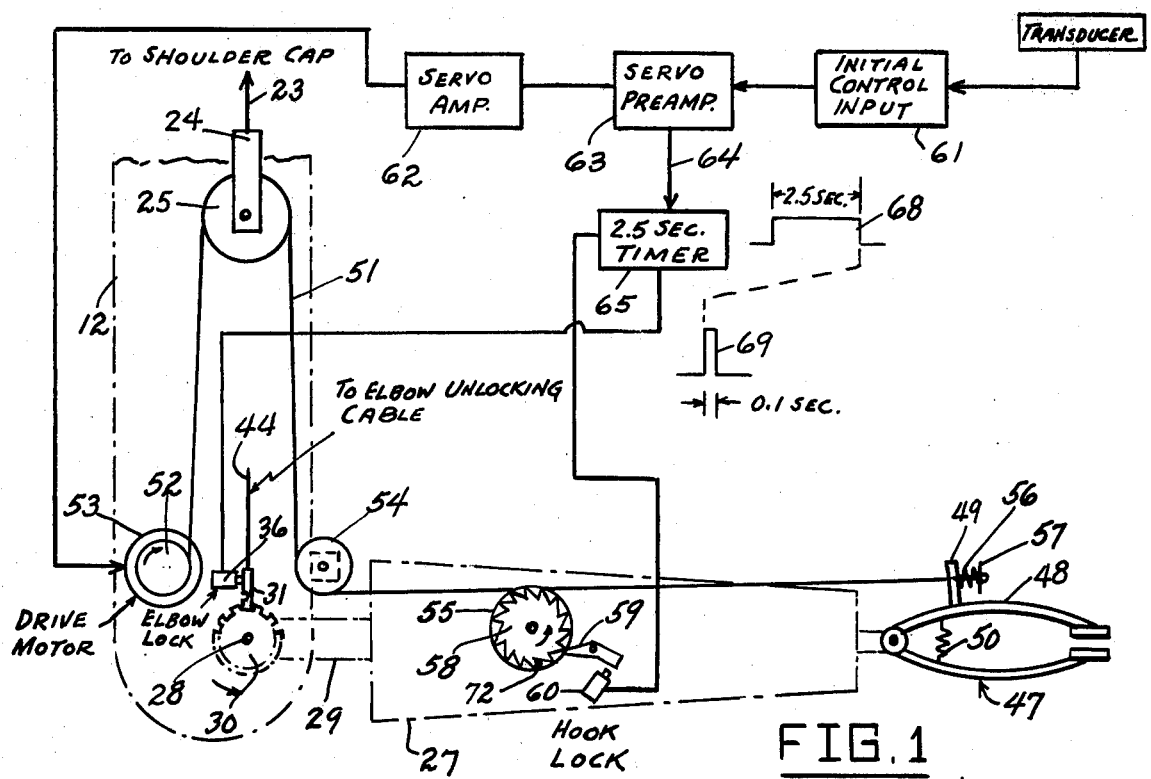
FIG. 1 is a diagrammatic view of a portion of an electrically operated prosthetic unit provided with an improved hook locking device according to the present invention.

Referring to the drawings, and more particularly to FIG. 1, 12 diagrammatically designates the upper arm portion of a prosthesis, for example, of the type employing a shoulder cap, not shown, shaped to fit over an amputee's shoulder and provided with suitable fastening braces or straps connected to supports suitably secured on the wearer's body, the upper arm portion 12 being pivoted to said shoulder cap and having suitable means for releasably locking portion 12 against rotation.

A cable element 23 is connected at its top end to said shoulder cap and is supportingly connected at its other end to a pulley bracket 24 in which a pulley 25 is rotatably supported.

The forearm portion of the prosthesis, shown schematically at 27, is pivotally attached to the lower end of the upper arm member 12 by a pivot shaft 28 to define an elbow joint. For example, the shaft 28 may be rigidly secured to member 12 and forearm member 27 may be provided with an extension bar 29 rotatably engaged on shaft 28. Extension bar 29 is provided with a rigidly-connected toothed wheel 30 concentric with shaft 28 lockingly engageable by a radially disposed pawl member 31 suitably slidably supported in upper arm member 12. Pawl member 31 is suitably spring biased toward locking engagement with toothed wheel 30 but can be held disengaged therefrom by the spring-biased plunger of an elbow lock control solenoid 36. User-operated means is provided for at times retracting the pawl member 31 for allowing it to be latched in its retracted position by means of said solenoid plunger, so as to unlock the elbow joint, for example, a connection element 44 adapted to be attached to an elbow unlocking cable. The elbow becomes locked when solenoid 36 receives a release pulse 69 and retracts its plunger, as will be presently described.

A conventional terminal device, such as a hook assembly 47, is provided on the forward end of the forearm portion 27, said assembly 47 having the upper pivoted element 48 provided with the operating lug 49. Hook assembly 47 is biased toward closing or gripping condition in a conventional manner by relatively strong spring means 50.

An operating cable 51 extends from a cable reel 52 secured on the shaft of a drive motor 53 mounted in upper arm member 12 adjacent the elbow joint. Cable 51 extends over pulley 25 and beneath an idler pulley 54 journalled on the upper arm member 12 forwardly adjacent the elbow joint. Said cable 51 extends a full turn around an idler pulley 55 journalled in forearm member 27, being secured to said idler pulley at 72, and is resiliently connected to hook-operating lug 49, Thus, cable 51 extends through the lug 49 and a, compliance spring 56 and is anchored to an end retaining washer 57 in the manner diagrammatically illustrated in FIG. 1.

Idler pulley 55 is provided with an integral ratchet wheel 58 lockingly engageable by a pivoted pawl 59 provided on forearm member 27 and controlled by a hook lock solenoid 60 mounted on member 27, for at times locking the cable 51 relative to the hook-opening lug 49, as will be presently described.

Compliance spring 56 is relatively stiff, so that the tension developed in cable 51 by the operation of motor 53 will not be sufficient to open hook assembly 47 unless both the shoulder and elbow joints are locked.

It will be seen that the motor 53 is energized responsive to and in accordance with an appropriate signal generated in an "initial control input" stage, designated at 61. This signal may be derived in any suitable manner as a controlled proportional response to a specific muscular command movement of the user, for example, as an EMG signal obtained from a conventional muscle skin sensor. Alternatively, a magnetic motion detector may be used to provide a proportional signal by suitably coupling the appropriate skin motion to a transducer. Any suitable conventional body-powered signal generating system may be employed. The power source may comprise a battery conveniently carried by the user, for example, a battery supported from the user's belt.

The signal output of initial stage 61 is furnished to a servo amplifier 62 through a servo peramplifier 63. Motor 53 is driven by the output of servo amplifier 62.

Servo preamplifier 63 has an auxiliary output at 64 which is employed to generate an operating (lock release) signal, for the elbow lock solenoid 36 at a predetermined time after motor 53 becomes energized, for example, after 2.5 seconds, considered sufficient to provide the desired amount of lifting movement of forearm portion 27 with respect to upper arm member 12. Thus, the output line 64 is connected to solenoid 36 through a 2.5 second timer 65, typically illustrated in detail in FIG. 3.

Figure 2:
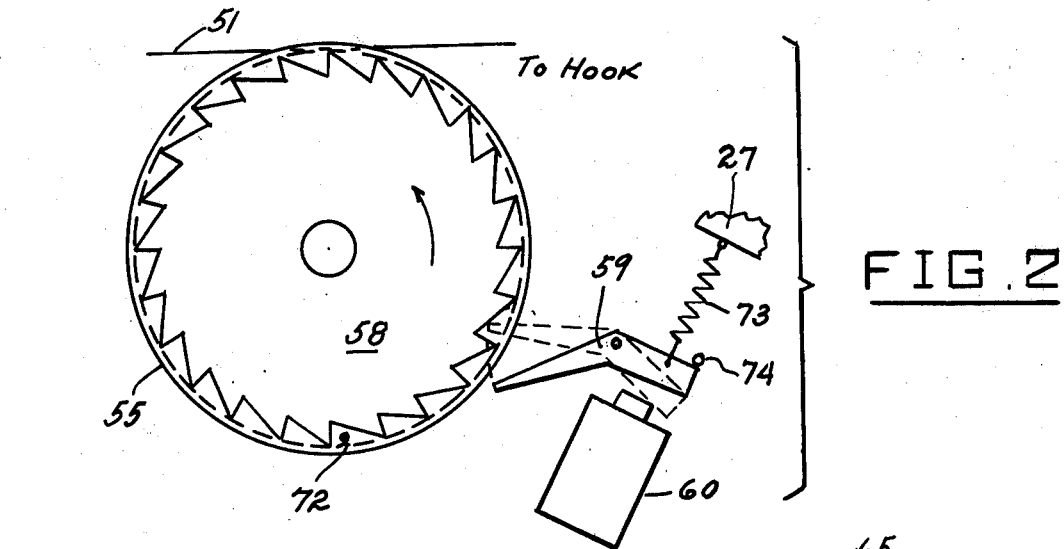
FIG. 2 is an enlarged elevational view of the pawl and ratchet assembly employed in the prosthetic unit of FIG. 1.
Figure 3:
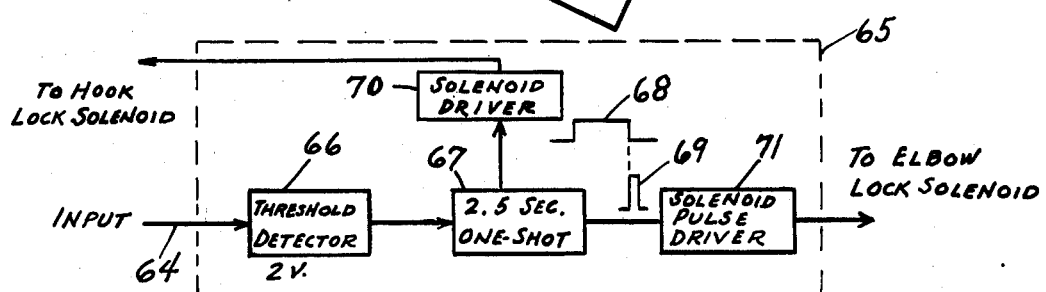
FIG. 3 is a block diagram of the locking timer circuit employed in the prosthetic unit of FIG. 1.

In the typical example illustrated in FIG. 3, the line 64 is connected through a 2-volt threshold detector 66 of conventional design to the input of a conventional 2.5 second one-shot 67 which generates a 2.5 second main internal pulse 68 and a 0.1 second output pulse 69 at the end of said main pulse. The main pulse is supplied through a solenoid driver stage 70 to the hook lock solenoid 60, whereby the ratchet wheel 58 is locked by pawl 59, which is rotated by solenoid 60 against the biasing force of a pawl spring 73 to the dotted view position thereof shown in FIG. 2, from its normal nonlocking position engaging a stop pin 74. This allows a slight amount of counterclockwise rotation (as viewed in FIGS. 1 and 2) of ratchet wheel 58 as it locks against pawl 59. This places some tension on compliance spring 56.

Thus, ratchet wheel 58 is locked during the 2.5 second lifting period of forearm portion 27, preventing cable 51 from opening the grasping hook assembly 47.

Pawl 59 lockingly engages the teeth of ratchet wheel 58 and is held in locking engagement as long as there is torque on forearm member 27, namely, as long as there is steady tension on cable 51 urging pulley 55 counterclockwise, as viewed in FIGS. 1 and 2. Pawl 59 will be released after the conclusion of pulse 68 and the relaxation of tension on cable 51.

Thus, ratchet wheel 58 is released at the end of the 2.5 second period defined by pulse 68 by the following action: at the end of said 2.5 second period, the short pulse 69 is supplied through a solenoid driver stage 71 to the elbow lock solenoid 36, retracting its plunger and releasing the pawl member 31, causing said pawl member 31 to move to its elbow locking position, shown in FIG. 1. With the load now supported by the elbow lock, the tension on cable 51 can be relaxed sufficiently to allow spring 56 to rotate ratchet wheel 58 clockwise sufficiently to permit pawl 59 to clear its ratchet teeth and to permit said pawl to return to its normal disengaged position by the action of spring 73. Thereafter, the energization of motor 53 can be increased to a degree to develop sufficient tension in cable 51 to open the hook assembly 47.

To release the forearm portion 27 it is merely necessary to unlock the elbow by means of its unlocking cable, namely, to retract the pawl 31, and allow forearm portion 27 to return to its normal depending position by gravity. The elbow will remain unlocked by the latching of pawl member 31 in its elevated position by the springbiased plunger of solenoid 36.

With the elements 12 and 27 in normal depending positions, the elbow joint is normally unlocked. To elevate forearm portion 27, a command signal is applied to the control input stage 51, causing motor 53 to be energized and triggering the timer 65. The hook lock solenoid 60 is energized by the pulse 68, locking the hook assembly 47 while the forearm portion 27 is elevated to a desired position under the control of the command signal. After the 2.5 second timed period, solenoid 36 is pulsed and releases pawl member 31, causing the elbow joint to be locked in said desired position. Hook lock solenoid 60 becomes deenergized, enabling the release of the hook assembly by a reduction in motor torque on ratchet wheel 58, as above described, which allows pawl 59 to disengage from ratchet wheel 58. Further actuation of motor 53 (the shoulder and elbow joints being locked) causes opening of the hook assembly 47 by the tension developed in cable 51.

While a specific embodiment of an improved prosthetic load-lift hook locking mechanism has been disclosed in the foregoing description, it will be understood that various modifications within the scope of the invention may occur to those skilled in the art. Therefore it is intended that such modifications and adaptations are within the meaning and range of equivalents of the disclosed embodiment and may be made without departing from the invention.

What is claimed is:

1. In an artificial limb unit, an upper arm portion, a forearm member pivoted to said upper arm portion to define an elbow joint, a terminal device on the end of said forearm member, a drive motor on said upper arm portion, means to energize said motor, power transmission means drivingly interconnecting said motor, forearm member and terminal device for elevating said forearm member, and means on said forearm member locking said terminal device while the forearm member is being elevated by said motor; said power transmission means comprising a cable and pulley system operatively coupling said motor, forearm member and terminal device; said cable and pulley system including a cable portion extending along said forearm member toward said terminal device and being operatively connected to said terminal device; and said means locking the terminal device comprising means locking said cable portion against movement while the forearm member is being elevated, which comprises a ratchet wheel journalled on said forearm member, means coupling said cable portion to said ratchet wheel, movable pawl means on the forearm member lockingly engageable with said ratchet wheel, and pawl operating means for lockingly engaging said pawl means with said ratchet wheel during the elevation of said forearm member.

2. The artificial limb unit of claim 1, and wherein said cable portion is engaged concentrically around and is fastened to said ratchet wheel.

3. The artificial limb unit of claim 1, and wherein said terminal device comprises a hook assembly having relatively pivoted grasping members and means biasing said grasping members toward closing positions, one of said grasping members having an operating lug for opening the grasping members, and means resiliently connecting said cable portion to said operating lug for allowing close interlocking cooperation of the ratchet wheel with said pawl means during the elevation of said forearm member.

4. The artificial limb unit of claim 1, and wherein said pawl operating means comprises an electromagnet located to urge said pawl means into locking enegagement with the ratchet wheel responsive to energization of the electromagnet, and means to energize said electromagnet for a timed period commencing with the energization of said motor.

5. The artificial limb unit of claim 1, and wherein said pawl operating means comprises electromagnetic means operatively coupled to said pawl means, and means to energize said electromagnetic means concurrently with the energization of the motor to elevate said forearm member.

6. The artificial limb unit of claim 5, and wherein said forearm member is provided with elbow locking means, means to activate said elbow locking means at the end of a timed period of energization of said motor, and means to deenergize said electromagnetic means concurrently with the activation of said elbow locking means.

7. The artificial limb unit of claim 6, and wherein said means to energize said electromagnetic means comprises a one-shot timed pulse forming device connected to said electromagnetic means, and operating circuit means connecting said motor energizing means to said pulse forming device.

* * * * *